(12) United States Patent
Fenske et al.

(10) Patent No.: US 10,602,792 B2
(45) Date of Patent: Mar. 31, 2020

(54) METHOD FOR MANUFACTURING ELASTIC PANTS

(71) Applicant: ELASTEC SUISSE AG, Waedenswil (CH)

(72) Inventors: Wilfried Fenske, Waedenswil (CH); Sandra Fenske, Waedenswil (CH)

(73) Assignee: ELASTEC SUISSE AG, Waedenswil (CH)

( * ) Notice: Subject to any disclaimer, the term of this patent is extended or adjusted under 35 U.S.C. 154(b) by 207 days.

(21) Appl. No.: 15/531,448

(22) PCT Filed: Dec. 1, 2015

(86) PCT No.: PCT/EP2015/078210
§ 371 (c)(1),
(2) Date: Jun. 21, 2017

(87) PCT Pub. No.: WO2016/087440
PCT Pub. Date: Jun. 9, 2016

(65) Prior Publication Data
US 2018/0168262 A1 Jun. 21, 2018

(30) Foreign Application Priority Data

Dec. 4, 2014 (DE) .................. 10 2014 117 935

(51) Int. Cl.
*A41H 42/00* (2006.01)
*A41H 43/02* (2006.01)
(Continued)

(52) U.S. Cl.
CPC .............. *A41H 42/00* (2013.01); *A41B 9/00* (2013.01); *A41B 9/001* (2013.01); *A41B 9/02* (2013.01);
(Continued)

(58) Field of Classification Search
CPC .......... A61F 13/15593; A61F 13/15601; A61F 13/1565; A61F 13/15658; Y10T 156/101;
(Continued)

(56) References Cited

U.S. PATENT DOCUMENTS

| 2008/0156418 A1* | 7/2008 | Fenske .............. A61F 13/15593 156/161 |
| 2013/0011601 A1* | 1/2013 | Fenske .............. A61F 13/15593 428/101 |

FOREIGN PATENT DOCUMENTS

| DE | 20051115754 A1 | 12/2005 |
| DE | 102010013288 A1 | 9/2011 |

(Continued)

OTHER PUBLICATIONS

International Search Report (dated Apr. 22, 2016) for corresponding International App. PCT/EP2015/078210.

*Primary Examiner* — Carson Gross
(74) *Attorney, Agent, or Firm* — WRB-IP LLP

(57) ABSTRACT

The invention relates to a method for continuously manufacturing elastic pants (28), wherein a flat web material (1, 16, 19) is continuously conveyed in a longitudinal direction (8) of the web material (1, 16, 19), is shaped into a closed tube (4), and is closed in the longitudinal direction (8). The closed tube (4) forms a first outer layer (9). Elastic threads (10) in the form of a tubular reinforcement are then wound around the first outer layer (9) in the conveying direction (8) in such a way that the elastic threads (10) are taut when the outer layer (9) has a convex shape. A second outer layer (15) is then continuously applied to the elastic threads (10) in the conveying direction (8) and is joined to the elastic threads (10) and/or the first outer layer (9). The first outer layer (9), the elastic threads (10) and the second outer layer (15) form an elastic pants web material (21). Further down in the conveying direction (8), the pants web material (21) is
(Continued)

closed along a joining section (29) in regular intervals such that the joining section (29) forms two approximately equally large opening sections that lie opposite each other in the transverse direction. Further down in the conveying direction (8), the pants web material (21) is cut at a distance from the joining section (29) such that a pair of elastic pants (28) is formed.

15 Claims, 4 Drawing Sheets

(51) Int. Cl.
| | |
|---|---|
| *A41D 1/06* | (2006.01) |
| *A41B 9/00* | (2006.01) |
| *A41D 31/02* | (2019.01) |
| *A41B 9/02* | (2006.01) |
| *A41B 17/00* | (2006.01) |
| *A41H 43/04* | (2006.01) |
| *B32B 1/08* | (2006.01) |
| *B32B 5/02* | (2006.01) |
| *B32B 5/26* | (2006.01) |
| *B32B 7/12* | (2006.01) |
| *B32B 37/02* | (2006.01) |
| *B32B 37/12* | (2006.01) |
| *B32B 37/24* | (2006.01) |
| *B32B 37/28* | (2006.01) |
| *B32B 38/00* | (2006.01) |
| *B32B 38/18* | (2006.01) |
| *A61F 13/15* | (2006.01) |
| *B29C 53/58* | (2006.01) |

(52) U.S. Cl.
CPC ................ *A41B 17/00* (2013.01); *A41D 1/06* (2013.01); *A41D 31/02* (2013.01); *A41H 43/0235* (2013.01); *A41H 43/04* (2013.01); *B32B 1/08* (2013.01); *B32B 5/02* (2013.01); *B32B 5/022* (2013.01); *B32B 5/26* (2013.01); *B32B 7/12* (2013.01); *B32B 37/02* (2013.01); *B32B 37/1284* (2013.01); *B32B 37/24* (2013.01); *B32B 37/28* (2013.01); *B32B 38/0004* (2013.01); *B32B 38/1858* (2013.01); *B32B 38/1866* (2013.01); *B32B 38/1875* (2013.01); *A41B 2400/38* (2013.01); *A41B 2500/30* (2013.01); *A41D 2400/38* (2013.01); *A41H 43/0257* (2013.01); *A61F 13/1565* (2013.01); *A61F 13/15593* (2013.01); *A61F 13/15601* (2013.01); *A61F 13/15658* (2013.01); *B29C 53/58* (2013.01); *B32B 2250/20* (2013.01); *B32B 2255/02* (2013.01); *B32B 2305/10* (2013.01); *B32B 2307/51* (2013.01); *B32B 2309/16* (2013.01); *B32B 2437/00* (2013.01); *B32B 2555/02* (2013.01); *Y10T 156/101* (2015.01); *Y10T 156/1013* (2015.01)

(58) Field of Classification Search
CPC .............. Y10T 156/1013; B29C 53/58; B32B 2555/02
USPC ......................................................... 156/195
See application file for complete search history.

(56) References Cited

FOREIGN PATENT DOCUMENTS

| GB | 1108777 A | * 4/1968 | ............. A41B 13/04 |
|---|---|---|---|
| GB | 1250788 A | 10/1971 | |

* cited by examiner

METHOD FOR MANUFACTURING ELASTIC PANTS

BACKGROUND AND SUMMARY

The invention concerns a method for manufacturing elastic pants.

It is known from the prior art to manufacture elastic pants, and especially elastic underwear, from surface elastic materials. By using such surface elastic materials, the underwear, which is usually located close to the skin, is made noticeably more comfortable to wear, as the underwear sits well, while at the same time exerts comparatively low surface pressure on the body, as the force-fit connection to the skin over the entire contact surface of the underwear necessary for the underwear to hold in the way required and sit properly is achieved.

A method for manufacturing such a surface elastic textile material, that can especially be used to manufacture underwear, is described in the publication EP 1 753 618 B1. With this method, a plan web material is continuously transported in a longitudinal direction of the web material and folded over an elongated rod-like or tubular shaping core into a convex tubular closed form. The tube formed in this way forms a first outer layer, to the outer surface of which elastic threads are applied in the form of a tubular reinforcement, wherein the elastic threads are prestressed when they are applied to the first outer layer, so that, if the first outer layer or the tube is removed from the shaping core, the first outer layer is tapered by forces impacting on the tube from the elastic threads in a radial direction of the tube.

A second outer layer is subsequently likewise applied to the elastic threads from a plan web material, and connected with the elastic threads. The tubular web material formed in this way is thereupon cut open in a longitudinal direction, wherein only the elastic threads need to be severed, as the first outer layer folded in a tubular form and the second outer layer are placed, in relation to one another, in such a way that the tubular web material can be cut open along a line, whereby the end sections of the first outer layer, as well as the second outer layer are always adjacent to one another. In this way, the tubular web material can be unfolded along said line to form a surface elastic web material once the elastic threads have been severed, and may, for example, subsequently be processed to produce underwear.

With the methods known from the prior art, in order to manufacture the underwear, the surface elastic web material is initially manufactured and this is then subsequently processed further in additional stages of processing, in a known way, to create underwear.

It is desirable to continue to develop the elastic pants made out of a surface elastic material, known from the prior art, in such a way that the elastic pants can be easily and cost-effectively manufactured in a single manufacturing process.

In accordance with an aspect of the invention a method is provided for continuously manufacturing elastic pants wherein a plan web material is continuously transported in a longitudinal direction of the web material, is formed into a tube and is closed in the longitudinal direction, wherein the closed tube forms a first outer layer and wherein the first outer layer subsequently wound around with elastic threads in the transport direction in the form of a tubular reinforcement, so that the elastic threads are taut when the outer layer has a convex shape, wherein a second outer layer subsequently and continuously applied to the elastic threads in the transport direction and connected to the elastic threads and/or the first outer layer, wherein the first outer layer, the elastic threads and the second outer layer form an elastic web material for pants, characterized in that subsequently the wet material for pants is closed at regular intervals along a joining section, so that two opening sections of approximately the same size are formed by the joining section in transverse direction as to oppose one another, and wherein subsequently the web material for pants is cut at a distance to the joining sections in the transport direction, thereby forming elastic pants.

Use is made of the method for manufacturing surface elastic materials known from the prior art and described at the beginning, when manufacturing the elastic pants, wherein, unlike with that method, the first outer layer is, for example, sealed by welding, an adhesive bond or similar, whereas, with the method known from the prior art, the elastic web material is merely folded to form the tube, wherein the end sections of the elastic web material lie adjacent to one another and are not connected to one another. In order to seal the tube, the tube can either be formed in such a way that the end sections of the unfolded web material overlap with one another and the overlapping end sections are connected with one another in the area of overlap, or can also be manufactured by the web material being folded in such a way that lateral edges of the folded web material lie adjacent to one another and the end sections adjoining the lateral edges are, for example, connected to one another by a seam or similar. According to the invention, it is provided for that the second outer layer can also be sealed in a comparable way.

The web material is preferably a non-woven material, a web material, a film or a multi-layer laminate from this or comparable materials. The elastic threads used to manufacture the tubular reinforcement can, according to the invention, be manufactured, among other things, from spandex, rubber, synthetic rubber or comparable materials.

When the elastic threads are arranged on the first outer layer, it is possible to either resort to the method known from the prior art, involving the first outer layer being brought into a convex shape and the elastic threads being applied to the first outer layer under prestress. It is, however, also possible to taper the first outer layer, and apply the elastic threads to the tapered outer layer, either without any prestressing or with only a small amount of prestressing.

According to the invention, the second outer layer is manufactured from a plan web material, wherein comparable materials can be used, which are also used to manufacture the first outer layer.

The pants are manufactured from the web material for pants, by the web material for pants being sealed along the length of the joining section at regular intervals. The sealing along the joining section may be performed using welding, adhesion or similar. In the process, interior surfaces of the first outer layer are connected with one another in the joining section.

It is expedient for the connection in the joining section to be designed in a linear fashion, and preferably show an arched contour. When the pants manufactured with the help of the method in accordance with the invention are worn, the connection occurs in the stride of the person wearing the pants, so that, as per the invention, the arched contour is adapted to the body contour in this area.

Through the connection in the joining section, the web material for pants is sealed in the transverse direction, i.e. transverse to the direction of transport of the web material for pants, in such a way that the tubular web material for pants in the section in which the joining section is located, is divided by the connection into two tubular areas.

In order to manufacture the pants, the web material for pants sealed in the joining section is severed at a distance to the joining section, as a result of which the elastic pants are formed. The severing can be performed using a contoured profile adapted to the shape of the body, in order to be able to manufacture various different models of pants, such as underpants or boxer shorts. Through the web material for pants being severed at regular intervals, pants are constantly being manufactured in the course of the manufacturing process.

In order to simplify the manufacture and save on material, it is provided for by the invention that the web material is severed between two inversely designed joining sections, that are manufactured at a distance to one another, so that two inversely designed pairs of pants are manufactured in each case.

In order to connect the first outer layer, the elastic threads and the second outer layer with one another, it is provided for, in accordance with the invention, that an adhesive is applied to the elastic threads. It is, however, also possible and provided for in accordance with the invention to connect the second outer layer with the first outer layer, for example by welding or similar, wherein the connecting points used for this are designed in such a way that the elastic effect of the elastic threads is not impaired. According to the invention, the various different connections possible can also be combined, so that a welding connection can, for example, be used in addition to an adhesive connection.

It is advantageously provided for, in accordance with the invention, that the web material for pants is continuously spread and pulled in a flat shape before producing the joining section. The joining section can, in this way, be manufactured in an especially simple way, such as through welding. In the case of the web material for pants pulled into the flat shape, the joining section is placed in a central area between two longitudinal sides of the web material for pants running in the longitudinal direction of the web material for pants.

In the case of a further advantageous embodiment of the method in accordance with the invention, it is provided for that the first outer layer and the elastic threads are continuously spread and pulled in a flat shape before applying the second outer layer. The arrangement of the second outer layer on the elastic threads can, in this way, be simplified considerably.

In order to be able to simply place the second outer layer on the first outer layer pulled into the flat shape, it is, according to the invention, provided for that the second outer layer is produced from two sublayers, wherein the two sublayers are applied to opposite sides of the spread first outer layer and the elastic threads. The sublayers can be manufactured from an elastic web material by separating off the elastic web material or by unfolding the elastic web material along a central line running between the longitudinal sides of the elastic web material. It is, however, also possible, and provided for in accordance with the invention, that different webs of a web material can be used for manufacturing the sublayers wherein different web materials can also be used to advantage, for example to make different properties of the front of a pair of pants and the back of a pair of pants possible.

In order to further influence the properties of the elastic pants, it is provided for, in accordance with the invention, that elastic threads are also applied to the second outer layer in the form of a tubular reinforcement and a third outer layer is applied to these elastic threads. The third outer layer and the elastic threads can, in turn, be manufactured from the same materials as the first and second outer layers, as well as the elastic threads already used and applied to the first outer layer. The first outer layer, the second outer layer, the third outer layer and the elastic threads located between the layers constitute the web material for pants. The third outer layer can, according to the invention, be processed in the same way as the first and second outer layers.

The method in accordance with the invention is also suitable for manufacturing disposable diapers or similar. In particular in this respect, it is provided for, in accordance with the invention, that a granular material and/or a fibrous material is arranged between the first outer layer and the second outer layer and/or between the second outer layer and the third outer layer. The granular material may, according to the invention, concern a superabsorber, which can take up a comparatively large quantity of liquid.

According to the invention, it is in particular provided for, in regard to the manufacture of disposable diapers, that the first outer layer and/or the second outer layer and/or the third outer layer is manufactured from a hydrophobic or a hydrophilic material. The properties of the disposable diapers can be influenced in this way, because it can be achieved, by making a suitable choice of the material used to manufacture the layers, that moisture from the person wearing the disposable diapers is quickly transported from his or her body in the direction of the second outer layer or the third outer layer, wherein it can simultaneously be avoided that moisture leaks out of the second outer layer or the third outer layer or back to the first outer layer, and is transported through the first outer layer.

In order to achieve a sufficient surface elasticity of the pants manufactured, it is provided for, in accordance with the invention, that a length of the elastic threads corresponds to 120% to 500% of the length of the elastic threads in the untensioned state, if the first outer layer has a convex shape. The convex shape, within the meaning of this invention, is characterized in that the first outer layer is fully spread out, so that all the connecting lines of two points of a perimeter running in a transverse direction of the first outer layer nm entirely within said perimeter.

In order to be able to influence the surface elasticity of the pants manufactured on an area-by-area basis, it is provided for, in accordance with the invention, that at least one elastic thread consists of or comprises a material different from that of the remaining elastic threads. For example, threads of differing elasticity can be used, wherein some threads can be provided for to improve the stability and durability of the pants manufactured, and other threads can serve the purpose of providing the necessary surface elasticity.

In order to manufacture the tubular first outer layer, it is provided for, in accordance with the invention, that the plan web material is continuously folded in the longitudinal direction of the web material to form the closed tube over an elongated shaping core, wherein the shaping core is designed in such a way that the tube has a convex shape.

It is, according, to the invention, advantageously provided for that a shape of the second outer layer and/or the third outer layer is adapted to the convex shape of the first outer layer and is thus applied to the elastic threads. According to the invention, the second outer layer and/or the third outer layer can, in a comparable way, be folded into a tubular form via the first outer layer folded over the shaping core and the elastic threads placed on the first outer layer.

It is advantageously provided for in accordance with the invention that the elastic threads are applied to the first outer layer and/or the second outer layer under prestress.

In order to be able to apply the elastic threads to the first outer layer, it is provided for, in accordance with the invention, that the elastic threads are wound on thread bobbins, wherein the thread bobbins are arranged on at least one planetary gear, wherein the first outer layer is guided through the planetary gear in the convex shape, wherein the planetary gear is caused to rotate around the first outer layer and wherein the elastic threads are continuously un-wound from the thread bobbins and applied to the first outer layer. By analogy, elastic threads can also be applied to the second outer layer.

A central axis of the planetary gear may, in accordance with the invention, run axially to a central axis of the tubular unfolded first outer layer running in the direction of transport. In order to influence the course or the direction of the elastic threads on the first outer layer, it is, however, also possible, and provided for in accordance with the invention, for the central axis of the planetary gear and the central axis of the first outer layer to be at an angle to one another. According to the invention, it is, in this way, possible for the elastic threads to run, on an area-by-area basis, in the transverse direction on the first outer layer. The planetary gear used to arrange the elastic threads on the second outer layer can be aligned analogously as well.

In order to influence the properties of the elastic pants, and especially in order to influence the surface elasticity of the pants, it is provided for, in accordance with the invention, that unwinding velocities are differentiated from one another when unwinding the elastic threads from different thread bobbins.

BRIEF DESCRIPTION OF THE DRAWINGS

Further advantageous embodiments of the method in accordance with the invention are explained in more detail based on embodiments shown in the drawing. The following are shown.

DETAILED DESCRIPTION

Figure 1:
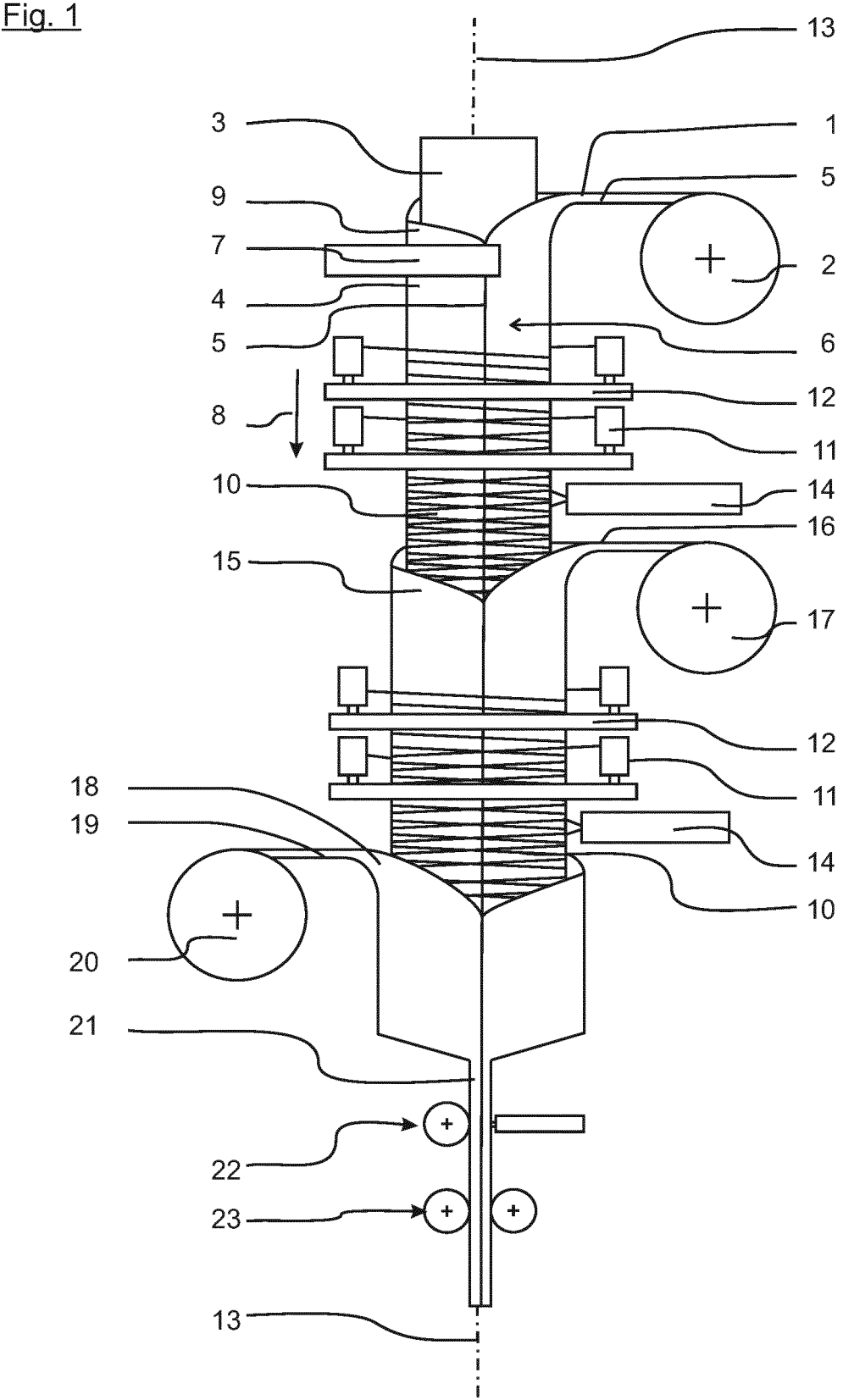
FIG. 1, a schematically shown view of the main functions and procedural steps when implementing the method for manufacturing pants in accordance with the invention.

FIG. 1 shows a schematic representation of the course of the method in accordance with the invention. A plan web material 1 is initially continuously unwound from a roll of material 2 and folded in a convex form to form a tube 4 over a shaping core 3. In the process, the web material 1 is folded in such a way that end sections 6 of the web material adjoining lateral edges 5 are arranged overlapping one another. Only one lateral edge 5 and one end section 6 are shown in the representation, as the second lateral edge and the corresponding second end section are to be found underneath the first end section 6, and are therefore not visible.

Once the plan web material 1 has been folded to form a tube 4, the tube 4 is sealed in the area of the end sections 6 in a longitudinal direction 8, using a welding device 7. The closed tube 4 forms a first outer layer 9. The first outer layer 9 is subsequently wound around the first outer layer 9 with elastic threads 10 in the form of a tubular reinforcement, in the longitudinal direction or direction of transport 8. The elastic threads 10 are wound off from thread bobbins 11, which are arranged on planetary gears 12. The planetary gears 12 are, for this purpose, set in rotation around the first outer layer 9 or the shaping core 3. A central axis or rotational axis of the planetary gears corresponds to a central axis 13 of the first outer layer 9.

Adhesive is subsequently applied to the elastic threads 10 using adhesive equipment 14. A second outer layer 15 is then subsequently applied to the elastic threads 10 in the direction of transport 8, wherein the second outer layer 15 likewise consists of or comprises a web material 16, that is unrolled from a roll of material 17.

The second outer layer 15 is subsequently once again wound around with elastic threads 10 in the direction of transport 8, the elastic threads 10 are sprayed with adhesive, and a third outer layer 18 is subsequently applied to the elastic threads 10 in this representation. The third outer layer 18 is, in turn, manufactured from a web material 19, which is unwound from a roll of material 20.

Finally, the web material for pants 21 manufactured in this way is pulled into a flat shape and sealed at regular intervals, always along a joining section, using a welding device 22, and subsequently severed at a distance to the joining section using a cutting device 23, as a result of which elastic pants are constantly being manufactured.

Figure 2:
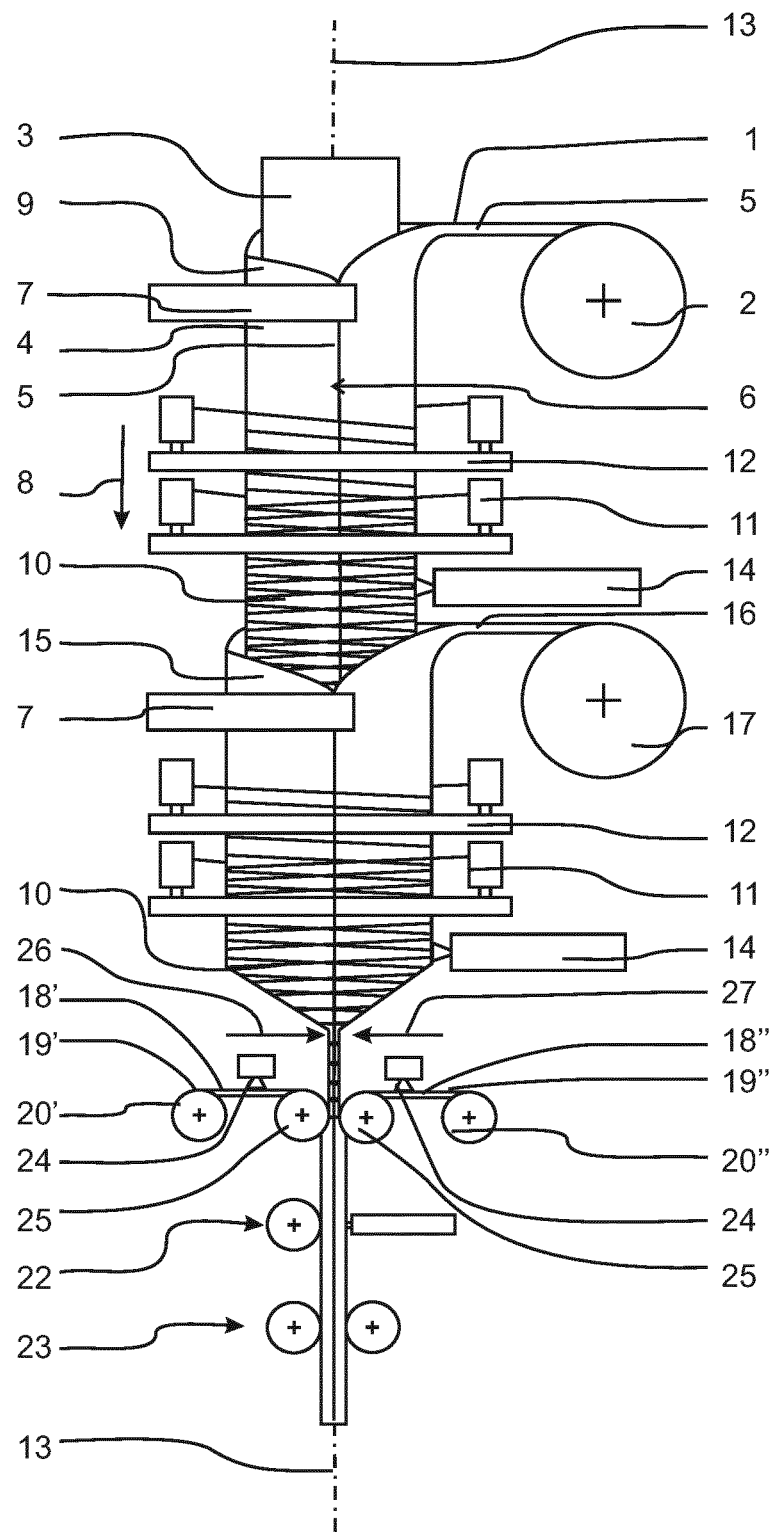
FIG. 2, a schematic representation of an alternatively designed method for manufacturing elastic pants, wherein a superabsorber is inserted between the second outer layer and the third outer layer.

In the course of the method in accordance with the invention shown schematically in FIG. 2, the first outer layer 9 and the second outer layer 15 are, prior to applying the third outer layer 18, pulled in a flat shape. When the third outer layer 18, which, in this embodiment, consists of or comprises two sublayers 18' and 18", which are each manufactured from separate web materials 19' and 19", and in each case unwound from rolls of material 20' and 20", is applied, a superabsorber 24 is applied to the sublayers 18' and 18" and held to the sublayers 18' and 18" by means of vacuum rolls 25 until the sublayers 18' and 18" are applied to the sides 26 and 27 of the tube 4 that has been pulled into a flat shape, located opposite one another. The further course of the manufacturing process corresponds to the course shown in FIG. 1.

The procedures schematically shown in FIGS. 1 and 2 can also be provided for in such a way that only the second outer layer 15 is applied and the third outer layer 18 is dispensed with, wherein, in the embodiment shown in FIG. 2, the superabsorber 24 can be applied to corresponding sublayers of the second outer layer 15.

Figure 3:
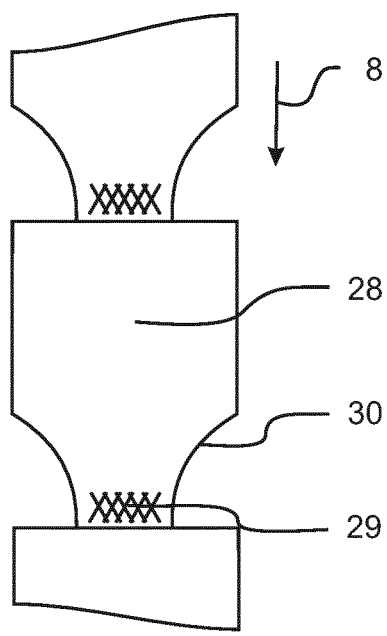
FIGS. 3 and 4, schematic representations of the elastic pants manufactured using the method in accordance with the invention.
Figure 4:
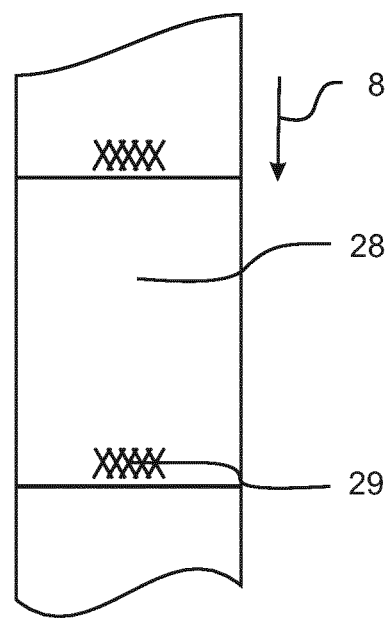

FIGS. 3 and 4 show schematic views from above onto multiple pants 28 manufactured using the method in accordance with the invention. The pants 28 have, in each case, been sealed in a joining section 29 by means of welding and subsequently disconnected along a cutting contour 30. In the case of the pants 28 shown in FIG. 3, the cutting contour 30 has been adapted to the shape of the body, while, in the case of the pants 28 shown in FIG. 4, a simple cut has been chosen, transverse to the longitudinal axis 8.

Figure 5:
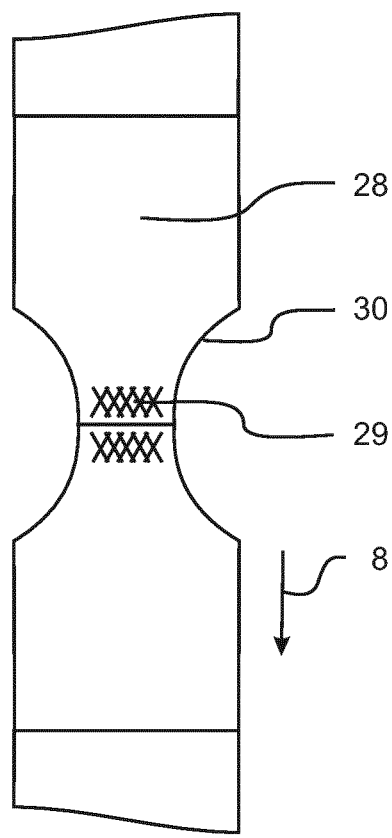
FIG. 5, a schematic representation of the pants manufactured using the method in accordance with the invention, wherein inversely designed joining sections have been arranged adjacent to one another and have, in this way, been manufacturing in pairs of inversely designed elastic pants.

In FIG. 5, elastic pants 28 manufactured in accordance with an alternative method are shown schematically, wherein the web material for pants 21 has been welded together in adjacent joining sections 29 that have been allocated to one another, during manufacture, and has subsequently been severed along a cutting contour 30, whereby pants 28 arranged inversely in pairs have been manufactured.

According to the invention, the pants 28 manufactured using the method are subsequently processed in further processing stages, and provided, for example, with suitable seams in the area of the cuts made.

Figure 6:
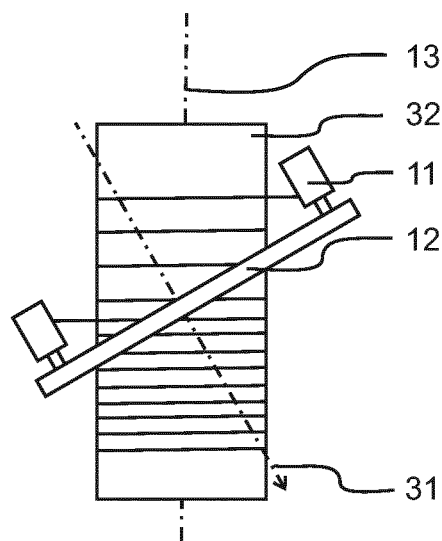
FIG. 6, a schematic representation of a planetary gear, the central axis of which is at an angle to the central axis of the first outer layer.
Figure 7:
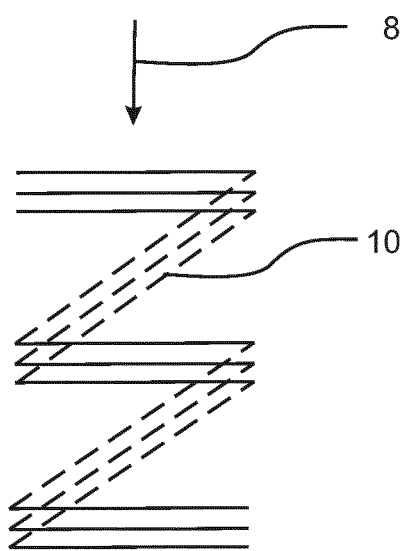
FIG. 7, a schematically portrayed course of the elastic threads applied to the outer layer with the help of the arrangement shown in FIG. 6.

In FIG. 6, an alternative arrangement of a planetary gear 12 is shown, wherein a central axis 31 of the planetary gear 12 is at an angle to a central axis 13 of an outer layer 32 to be wrapped round and pulled into a convex shape. The winding pattern or the course of the elastic threads 10 around the outer layer 32 shown there, shown schematically in FIG. 7 can, for example, be manufactured in this way. The elastic threads 10 run, in a section shown by a solid line, transverse to the longitudinal direction 8 of the outer layer 32, and in a second section, shown by a dotted line, at a slant to the longitudinal direction 8.

The invention claimed is:

1. Method for continuously manufacturing elastic pants, comprising
    continuously transporting a plan web material in a longitudinal direction of the web material,
    forming the plan web material into a closed tube and closing the plan web material in the longitudinal direction, wherein the closed tube forms a first outer layer,
    subsequent to forming the closed tube with the first outer layer, winding the first outer layer around with elastic threads in the longitudinal direction in the form of a tubular reinforcement, so that the elastic threads are taut when the outer layer has a convex shape,
    subsequent to winding the first outer layer around with elastic threads, continuously applying a second outer layer to the elastic threads in the longitudinal direction and connected to the elastic threads and/or the first outer layer, wherein the first outer layer, the elastic threads and the second outer layer form an elastic web material for pants,
    subsequent to forming the web material for pants, closing the web material for pants at regular intervals along a joining section, so that two opening sections of approximately the same size are formed by the joining section in transverse direction as to oppose one another, and
    subsequent to closing the web material for pants, cutting the web material for pants at a distance to the joining section in the longitudinal direction, thereby forming elastic pants.

2. Method according to claim 1, wherein an adhesive is applied to the elastic threads.

3. Method according to claim 1, wherein the web material for pants is continuously spread and pulled in a flat shape before producing the joining section.

4. Method according to claim 1, wherein the first outer layer and the elastic threads are continuously spread and pulled in a flat shape before applying the second outer layer.

5. Method according to claim 4, wherein the second outer layer is produced from two sub-layers, wherein the two sub-layers are applied to opposite sides of the spread first outer layer and the elastic threads.

6. Method according to claim 1, wherein elastic threads are also applied to the second outer layer in the form of a tubular reinforcement and a third outer layer is applied to these elastic threads.

7. Method according to claim 6, wherein a granular material and/or a fibrous material is arranged between the first outer layer and the second outer layer and/or between the second outer layer and the third outer layer.

8. Method according to claim 1, wherein a length of the elastic threads corresponds to 120% to 500% of the length of the elastic threads in a non-taut state, when the first outer layer has a convex shape.

9. Method according to claim 1, wherein at least one elastic thread comprises a material different from that of the remaining elastic threads.

10. Method according to claim 1, wherein the plan web material is continuously folded in the longitudinal direction of the plan web material into the closed tube over an elongated shaping core, wherein the shaping core is designed in such a way that the tube has a convex shape.

11. Method according to claim 10, wherein a shape of the second outer layer is adapted to the convex shape of the first outer layer and is thus applied to the elastic threads.

12. Method according to claim 10, wherein the elastic threads are applied to the first outer layer under prestress.

13. Method according to claim 10, wherein the elastic threads are wound on thread bobbins, wherein the thread bobbins are arranged on at least one planetary gear, wherein the first outer layer is guided through the planetary gear in the convex shape, wherein the planetary gear is caused to rotate around the first outer layer and wherein the elastic threads are continuously un-wound from the thread bobbins and applied to the first outer layer.

14. Method according to claim 13, wherein the planetary gear is oriented transversely to the longitudinal direction of the first outer layer.

15. Method according to claim 13, wherein un-winding speeds differ from one another when un-winding the elastic threads from different thread bobbins.

* * * * *